(12) United States Patent
Holland et al.

(10) Patent No.: US 10,456,483 B2
(45) Date of Patent: *Oct. 29, 2019

(54) GAS-ENCAPSULATED ACOUSTICALLY RESPONSIVE STABILIZED MICROBUBBLES AND METHODS FOR TREATING CARDIOVASCULAR DISEASE

(71) Applicant: University of Cincinnati, Cincinnati, OH (US)

(72) Inventors: Christy Holland, Cincinnati, OH (US); Himanshu Shekhar, Cincinnati, OH (US); Arunkumar Palaniappan, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/788,224

(22) Filed: Oct. 19, 2017

(65) Prior Publication Data

US 2018/0036437 A1  Feb. 8, 2018

Related U.S. Application Data

(63) Continuation-in-part of application No. 14/957,705, filed on Dec. 3, 2015.

(60) Provisional application No. 62/086,749, filed on Dec. 3, 2014.

(51) Int. Cl.
| | |
|---|---|
| *A61K 49/22* | (2006.01) |
| *A61K 49/00* | (2006.01) |
| *A61B 5/021* | (2006.01) |
| *A61N 7/02* | (2006.01) |
| *A61N 7/00* | (2006.01) |

(52) U.S. Cl.
CPC ........ *A61K 49/223* (2013.01); *A61K 49/0091* (2013.01); *A61K 49/221* (2013.01); *A61B 5/021* (2013.01); *A61N 7/022* (2013.01); *A61N 2007/0039* (2013.01)

(58) Field of Classification Search
None
See application file for complete search history.

(56) References Cited

U.S. PATENT DOCUMENTS

| | | | |
|---|---|---|---|
| 5,773,024 A | * | 6/1998 | Unger .................... A61K 8/046 424/450 |
| 5,837,221 A | | 11/1998 | Bernstein et al. |
| 6,146,657 A | | 11/2000 | Unger et al. |
| 7,976,743 B2 | | 7/2011 | Huang et al. |

FOREIGN PATENT DOCUMENTS

| | | |
|---|---|---|
| WO | 198604232 | 7/1986 |
| WO | 2014026117 A2 | 2/2014 |

OTHER PUBLICATIONS

Esra Talu, et al. Tailoring the Size Distribution of Ultrasound Contrast Agents: Possible Method for Improving Sensitivity in Molecular Imaging. Molecular Imaging, vol. 6, No. 6 (Nov.-Dec. 2007): pp. 384-392. (Year: 2007).*

* cited by examiner

*Primary Examiner* — Michael P Cohen
(74) *Attorney, Agent, or Firm* — Dinsmore & Shohl LLP (57) ABSTRACT

Acoustically responsive stabilized microbubbles formulated with a phospholipid monolayer shell, an encapsulated bioactive gas, and an encapsulated perfluorocarbon gas of the formula $C_xF_y$ in a volume ratio of from about 10:1 to about 1:10, wherein X is greater than or equal to 3, are disclosed. Also provided are methods for promoting localized vasodilation in a patient in need thereof by delivering a microbubble comprising a phospholipid monolayer shell and an encapsulated bioactive gas locally to a target diseased section of the patient's vasculature; and releasing the bioactive gas at the target diseased section, wherein the microbubble comprises the bioactive gas in a ratio of from about 10:1 to about 1:10 by volume with a perfluorocarbon gas.

10 Claims, 7 Drawing Sheets

GAS-ENCAPSULATED ACOUSTICALLY RESPONSIVE STABILIZED MICROBUBBLES AND METHODS FOR TREATING CARDIOVASCULAR DISEASE

RELATED APPLICATIONS

This application is a continuation-in-part of U.S. application Ser. No. 14/957,705, filed Dec. 3, 2015, and claims benefit under 35 U.S.C. § 119(e) to U.S. Provisional Application Ser. No. 62/086,749, filed Dec. 3, 2014, the entire disclosures of which are incorporated herein by this reference.

FEDERALLY SPONSORED RESEARCH OR DEVELOPMENT

This invention was made with Government support under R01 HL074002 awarded by the National Institute of Health. The Government has certain rights in the invention.

TECHNICAL FIELD

The subject matter of this application relates to gas-encapsulated acoustically responsive stabilized microbubbles and methods for promoting localized vasodilation in patients in need thereof. Specifically, the acoustically responsive microbubbles disclosed herein are useful in the treatment of diseases and conditions that benefit from promoting vasodilation, including cardiovascular disease, infective endocarditis, cerebrovascular disease, stroke, myocardial infarction, and the like.

BACKGROUND

Many diseases and conditions benefit from therapeutic promotion of vasodilation. Among these, cardiovascular disease (CVD) is currently the leading cause of death and is predicted to be the number one cause of disability worldwide by 2030 (World Health Organization 2014). In the United States, approximately 1 of every 4 deaths from 1999-2015 was due to CVD (Centers for Disease Control and Prevention, 2016). Ischemic heart disease and stroke were the leading primary causes of premature death. The overall economic impact of CVD was estimated to be $200 billion annually in the U.S., and is expected to increase in future decades. More effective diagnostic tools and therapies are necessary to limit the growing burden of CVD in the U.S. and worldwide, particularly the diseases which manifest in unwanted clotting within the arteries of the heart or brain.

A major contributor to acute cardiovascular events and sudden deaths is the development of atherosclerotic plaques, a progressive thickening of the arterial wall due to the accumulation of cholesterol. Rupture of atherosclerotic plaques can form thrombi that occlude blood flow, potentially leading to a life-threatening event. Thrombi occurring in the coronary artery can lead to a heart attack, and in cerebral arteries can lead to ischemic stroke.

The early detection and treatment of CVD is vital to assess the risk of vulnerable plaques leading to an acute cardiovascular event. However, screening for vulnerable atherosclerotic plaque using current imaging modalities poses specific challenges. Direct visualization using noninvasive imaging methods, e.g. carotid ultrasound, cardiovascular computed tomography, magnetic resonance imaging, and positron emission tomography, are preferable for early diagnosis of vulnerable atherosclerotic plaque in high-risk patients. For example, carotid ultrasound with measurement of the intima-media thickness within the artery wall offers a way to diagnose the extent of subclinical atherosclerotic vascular disease, assess risk, and may offer a means to identify disease progression and monitor the effectiveness of preventive therapies. The use of microbubble based ultrasound contrast agents as a complementary tool to enhance vascular ultrasound imaging, known as contrast-enhanced ultrasound imaging, is emerging as an important method in facilitating the detection and characterization of atherosclerotic disease.

The use of microbubbles as ultrasound contrast agents (UCAs) in vascular imaging is well established. Most commercially available UCAs consist of gas-filled microbubbles which have mean diameters between 1-5 µm and are encapsulated with a protein, polymer, or lipid shell. Albunex® (GE Healthcare) was the first UCA approved by the U.S. Food and Drug Administration and consisted of an air-filled microbubble encapsulated by an albumin shell. Second generation UCAs such as Optison® (GE Healthcare), Definity® (Lantheus Medical Imaging) and Lumason® (Bracco Diagnostics, Inc.) contain high-molecular-weight gases (e.g. $C_3F_8$ and $SF_6$ respectively), which have lower solubility in blood and thus increase the lifetime of the microbubbles in circulation. The low density and high compressibility of the gas core in UCAs enables efficient ultrasound scattering. Thus, the injected agents are acoustically responsive, or echogenic, and function as intravascular tracers which can be visualized using ultrasound.

In addition to traditional contrast-enhanced ultrasound imaging, there has been recent interest in advancing the applications of UCAs for molecular imaging of atherosclerosis. Molecular imaging techniques with targeted UCAs are being used increasingly for noninvasive diagnosis of inflammation, thrombus, and neovascularization. Targeted microbubble agents are also being developed for controlled drug-delivery applications and have been vigorously promoted for therapeutic applications in the treatment of CVD. Targeted UCAs are functionalized by engineering the gas-encapsulating shell to contain molecules that adhere to cells, which express disease-specific markers (e.g., aminoacids) on the membrane. Phospholipid-shelled UCAs are of particular interest for this purpose, because they can be targeted to molecular components of disease by attaching specific ligands to the surface.

Phospholipid-shelled UCAs represent one type of UCA that is currently available for clinical use. The lipid molecules employed in the formulations are typically amphiphilic molecules which spontaneously form micelle structures that can encapsulate a gas microbubble in an aqueous environment. The lipids are surface-active molecules (surfactants) that orient their hydrophilic polar groups outside towards the surrounding aqueous medium and their hydrophobic tails inside away from the water, stabilizing the microbubble and largely preventing the gas from escaping the encapsulation. Lipid-based ultrasound contrast agents such as Definity® and Lumason® (which was recently approved for clinical use in the U.S. but has been marketed as SonoVue® in Europe and Asia since 2001) are commercially available for diagnostic applications. MicroMarker® (VisualSonics, Toronto, Canada; Bracco Research SA, Geneva, Switzerland) and Targestar® (Targeson Inc., San Diego, Calif., USA) are examples of targeted phospholipid-shelled UCAs currently available for pre-clinical investigational use.

A more recent formulation in the broad category of phospholipid-shelled UCAs, known as echogenic liposomes (ELIP), has been developed which encapsulates both a gas and an aqueous phase (Alkan-Onyuksel et al. 1996; Huang et al. 2001). Standard liposomes are characterized by a phospholipid bilayer shell, which encapsulates an aqueous compartment. ELIP are said to be echogenic because they contain a gas microbubble that is highly reflective to ultrasound waves at low intensities. The exact location of the entrapped gas pockets in ELIP has not been fully ascertained, and may be due to gas pockets stabilized by lipid monolayers within the liposome, or within the lipid bilayer shell.

Targetable drug-delivery systems represent a fast developing area of nanotechnology and are expected to have a dramatic impact on medicine in the future. Many nano-scale drug carriers, such as liposomes, micelles, and polymer nanocapsules, have been developed or are under development for encapsulation and delivery of therapeutic drugs. Liposomes are a convenient, biologically compatible vehicle for administration of poorly soluble drugs, and are among the first generation of nano-scale drug delivery systems to be approved for clinical use and known as nanomedicines (Moghimi et al. 2005).

Gregoriadis and Ryman (1971) were the first to report on the use of liposomes as drug carriers for directed delivery. The authors hypothesized that encapsulation of enzymes within the aqueous inner compartment of liposomes would aid in directing the payload to a particular tissue and alleviate some of the problems associated with immunological response to the proteins in circulation. They found that liposomes remain largely intact during circulation and are cleared by lysosomes in the liver (and to a lesser extent in the spleen). Since then, liposome based drug-delivery systems have been developed using chemotherapeutic agents for cancer therapy, thromolytic agents, and genes, in addition to enzymes.

Most of the currently approved liposome formulations represent a basic form of nanomedicine involving a passive targeting and drug release process known as the enhanced permeability and retention (EPR) effect. This approach relies on extravasation and accumulation of the liposome-encapsulated drug at the target site, and is particularly suited for cancer therapy applications due to the enhanced vascular permeability of tumors compared with normal tissue. Because tumors are highly vascularized and often lack effective lymphatic drainage, liposomes tend to accumulate in tumors much more than they do in normal tissues, resulting in increased drug uptake in these regions. Although EPR is a rudimentary passive targeting method, it is a key reason liposomes are currently the most widely used drug nanocarrier in cancer therapy. To realize the drug delivery potential of liposomes for other applications fully, however, it is important to develop agents with an active triggering mechanism that allows the drug to be delivered in a more controlled fashion. Echogenic microbubbles, by virtue of their ability to encapsulate gas as well as therapeutic drugs, offer such a possibility.

Recently, ultrasound has been investigated as a method to trigger enhanced drug delivery within the human vasculature. The potential of ultrasound to control drug delivery spatially and temporally in a non-invasive manner is broadly appealing. Ultrasound-mediated drug delivery (UMDD) has been demonstrated in a number of tissue beds, for example the blood-brain barrier, cardiac tissue, prostate, and large arteries.

Acoustic cavitation is one physical mechanism that is hypothesized to influence UMDD. Cavitation as used herein refers to linear or nonlinear bubble activity that can occur near vessel walls within the vasculature upon ultrasound exposure, which can exert mechanical stress on nearby cells and junctions. Mechanical stress can disturb the barriers to drug delivery such as endothelial tight junctions or phospholipid membranes, via transient permeabilization. In vivo, cavitation can be nucleated at moderate acoustic pressure amplitudes (<0.5 MPa) by ultrasound contrast agents (UCAs).

Nitric Oxide (NO) is a gas molecule that dynamically modulates the physiological functions of the cardiovascular system, which include relaxation of vascular smooth muscle, inhibition of platelet aggregation, and regulation of immune responses. Because a reduced NO level has been implicated in the onset and progression of various disease states, NO is expected to provide therapeutic benefits in the treatment of cardiovascular diseases, such as essential hypertension, stroke, coronary artery disease, atherosclerosis, platelet aggregation after percutaneous transluminal coronary angioplasty, and ischemia/reperfusion injury. To date, pharmacologically active compounds that can release NO within the body, such as organic nitrates and sodium nitroprusside, have been used as therapeutic agents, but their efficacy is significantly limited by their rapid NO release, poor distribution to the target site, toxicity, and induction of tolerance. Attenuation of nitric oxide production in the etiology of atherosclerosis progression and diabetic vascular disease further highlights the need for novel therapeutic nitric oxide modulation and delivery strategies. Effective delivery of bioactive NO to target cardiovascular tissue remains a compelling need in the art.

Xenon is a gas molecule that induces robust cardioprotection and neuroprotection through a variety of mechanisms. Through its influence on $Ca^{2+}$, $K^+$, KATP/HIF, and NMDA antagonism, xenon is neuroprotective when administered before, during and after ischemic insults. Xenon has particular promise as a bioactive agent for the treatment of cerebrovascular diseases and conditions. However, effective delivery of bioactive xenon to target cardiovascular or cerebrovascular tissue remains a need in the art.

Hydrogen sulfide is an endogenously produced gasotransmitter involved in the regulation of nervous system, cardiovascular functions, inflammatory response, gastrointestinal system, and renal function. Hydrogen sulfide gas has therapeutic potential for diseases such as arterial and pulmonary hypertension, atherosclerosis, ischemia-reperfusion injury, heart failure, peptic ulcer disease, acute and chronic inflammatory diseases, Parkinson's and Alzheimer's disease, and erectile dysfunction. Effective delivery of bioactive hydrogen sulfide to target diseased sections of vasculature remains a need in the art.

Hence, the need exists for improved compositions and methods for targeted ultrasound-mediated delivery of therapeutic bioactive gases.

SUMMARY

Accordingly, the instant disclosure provides novel bioactive gas-loaded acoustically responsive stabilized microbubbles designed to exploit the benefits discovered upon intensive investigation of the properties and release profiles of microbubbles comprising various gases, combinations of gases, and ratios of specific gas combinations. Acoustically responsive stabilized microbubbles were formulated and properties and release profiles characterized to provide compositions and methods of promoting vasodilation in a patient that exhibit superior and unexpected benefits in the delivery and safe release of bioactive gases from microbubbles at target diseased vasculature sites. The stabilized microbubbles provide both diagnostic and therapeutic benefit.

One embodiment provides a method for promoting vasodilation in a patient in need thereof. The method comprises: delivering a stabilized microbubble comprising a phospholipid monolayer shell and an encapsulated bioactive gas locally to a target diseased section of the patient's vasculature; and releasing the bioactive gas at the target diseased section, wherein the microbubble comprises the bioactive gas in a volume ratio of from about 10:1 to about 1:10 with a perfluorocarbon gas.

Another embodiment is directed to a method of manufacturing an acoustically responsive microbubble effective for ultrasound-mediated drug delivery, the method comprising: providing a lipid dispersion comprising phospholipids in a sealed receptacle, evacuating air from a headspace of the sealed receptacle, injecting a volume ratio of a bioactive gas and a perfluorocarbon gas of the formula $C_xF_y$, into the headspace; and subjecting the receptacle to high-shear mixing, thereby providing a suspension comprising microbubbles loaded with the bioactive gas.

Still other embodiments are directed to acoustically responsive microbubbles comprising a phospholipid monolayer shell, an encapsulated bioactive gas selected from the group consisting of nitric oxide, hydrogen sulfide, and xenon gas, and an encapsulated perfluorocarbon gas of the formula $C_xF_y$, wherein X is greater than or equal to 3, and wherein the volume ratio of bioactive gas to $C_xF_y$ is from about 10:1 to about 1:10.

All references (e.g., printed publications such as books, papers, patents, patent applications, catalogs, databases) are incorporated herein by reference. In the event of a conflict or inconsistency, the present specification, as modified by any amendments thereto, shall control.

These and other embodiments will be more clearly understood by reference to the detailed disclosure and accompanying figures.

BRIEF DESCRIPTION OF THE FIGURES

FIG. 1. A schematic representation of the attenuation measurement setup is depicted. A pair of broadband PVDF transducers are employed to acquire the spectrum using a substitution technique. A pulser-receiver was used in through-transmission mode to generate the excitation pulse and amplify the received signal. Samples of UCAs in diluent or diluent alone were added to the reservoir and introduced into the sample chamber by gravity feed.

FIG. 5. Quantification of NO using an amperometric probe. Intact NOMB measurement denotes concentration of NO in the background. Broken NOMB measurement represents the overall measured concentration (NO that is encapsulated and dissolved in the background). (A) When 100% NO was used, no difference was obtained between the NO concentration measured with intact microbubbles and broken microbubbles. (B) The concentration of encapsulated NO was determined by subtracting background NO concentration amount from the overall concentration (n=5).

DETAILED DESCRIPTION

The clinical goal of liposomes designed for diagnostics and therapy is to deliver a pharmaceutical agent to the injured area. Liposomes are substantially spherical, self-assembling closed structures formed of concentric lipid bilayers with an aqueous phase inside and between the lipid bilayers. Their ability to entrap different water-soluble compounds within the inner aqueous phase and lipophilic agents between liposomal bilayers upon self-assembly has made them useful for delivery of different kinds of drugs and for carrying diagnostic agents in a variety of imaging modalities. It is known that modification of the liposome shell with polyethylene glycol (PEG) enhances circulation time and a common strategy is to attach antibodies or different binding moieties to the liposomal surface to target specific affected areas. Such modified liposomes are currently under investigation for targeted intravascular drug delivery to cells and noncellular components (such as endothelial cells, subendothelial structures, and blood components) as the targeted sites for diagnosing and treating cardiac pathologies, including myocardial infarction, coronary thrombosis, and atherosclerosis.

Myocardial infarction (MI) results from occlusion of coronary arteries by thrombi. During the ischemic phase and following reperfusion, extensive myocardial cell death occurs within the ischemic zone. The use of liposomes for delivery of MRI contrast agents and the use of PEG to increase circulation time (substantially by avoiding recognition by liver cells), as well as the incorporation of binding partners such as antibody onto the liposome surface to achieve targeted delivery, are all strategies known in the art. Visualization of thrombi and thrombolytic therapy are now mostly based on liposome-based targeted delivery of contrast agents and thrombolytic drugs, such as the enzymes urokinase, streptokinase, and tissue plasminogen activator (tPA).

A recent approach utilizes acoustically reflective (echogenic) liposomes (ELIP) that can be targeted to promote site-specific acoustic enhancement of either imaging or drug delivery. Ultrasound-mediated drug delivery is a relatively new technique for enhancing the penetration of drugs into diseased tissue beds noninvasively. By encapsulating drugs into microsized and nanosized liposomes, the therapeutic can be shielded from degradation within the vasculature until delivery to a target site by ultrasound exposure. For example, Doppler ultrasound treatment has been shown to result in earlier and more complete recanalization rates when tPA-loaded ELIP are co-administered. Echogenic liposomes have been used to further develop the targeted delivery of tPA and to investigate the effect of ultrasound exposure on thrombolytic efficacy. tPA is released from the nano-sized delivery complex when exposed to ultrasound.

Previous studies have suggested that encapsulating nitric oxide (NO) with other gas components may improve the delivery profile of NO; however an effective bioactive mixture with sufficiently reduced diffusion has yet to be designed. Perfluorocarbons, which are already known and approved as conventional ultrasound contrast agents due to their low solubility in aqueous media and their low diffusivity compared to low-molecular weight, biologically inert gases such as $N_2$, were an initially thought to provide a possible solution, in particular since NO is soluble in certain perfluorocarbons such as octafluoropropane (OFP). Thus, the presence of OFP would theoretically delay diffusion of NO out of the liposome. However early studies concluded that the trade-off in lowered bioactivity versus preventing free diffusion was not desirable, as very large radius liposomes would be required in order to accommodate the required encapsulation volume determined in the prior art.

The short half-life of bioactive gases such as NO due to hemoglobin scavenging has been an impediment to the therapeutic use of bioactive gases. Encapsulating a bioactive gas inside a lipid microbubble enables the gas to remain bioactive over a clinically relevant time frame. NO, for example, is a small molecule that can diffuse into surrounding fluid through a lipid bilayer or monolayer. Previous attempts to deliver NO to the bloodstream have used a liquid perfluorocarbon emulsion, and not a gas perfluorocarbon mixture (Rafikova, et al., *Control of plasma nitric oxide bioactivity by perfluorocarbons: Physiological mechanisms and clinical implications, Mol. Card.* 110: 3573-80 (2004). NO is also highly reactive and degrades quickly in the presence of oxygen. Previous research has shown that use of a sparingly soluble trapped species can significantly enhance emulsion stability. While not desiring to be bound by theory, one explanation is Raoult's law, where the chemical potential gradient for oxygen to dissolve into the microbubble in order to dilute the osmotic agent balances the chemical potential gradient for oxygen to dissolve out of the microbubble brought on by the capillary pressure (Taylor, *Ostwald ripening in emulsions, Advances in Colloid and Interface Science.* 75:107-63 (1998); Kabalnov, *Ostwald Ripening and Related Phenomena, Journal of Dispersion Science and Technology* 22: 1-12 (2001); Kwan, et al., *Theranostic oxygen delivery using ultrasound and microbubbles, Theranostics* 2: 1174-84 (2012)).

Octafluoropropane (OFP) belongs to a class of perfluorocarbons that are used alone as the gas phase in conventional ultrasound contrast agents, due to their low solubility in aqueous media and their low diffusivity. Combining NO with OFP enables a tradeoff between stability and therapeutic dose. The instant inventors have previously reported the feasibility of producing vasodilatation by delivery of NO into a viable carotid artery during exposure to ultrasound. The formulation employed a combination of the following lipids to encapsulate NO: Dipalmitoylphosphatidylcholine (DPPC), N-[1-(2,3-dioleoyloxy) propyl]-N,N,N-trimethylammonium (DOTAP), polyethylene glycol (PEG) 2000, and PEG 750 in a 79:15:3:3 molar ratio. Experience with this formulation revealed that NO alone could not be loaded within the microbubbles formed by the lipid shell. It was found that a 1:1 volume ratio of NO and OFP was sufficient to permit robust acoustic response while retaining bioactivity commensurate with standard-of-care vasodilators (Sutton et al. 2014). The instant inventors have now found that a different lipid formulation comprising DSPC encapsulates orders of magnitude higher gas payload than the previous DOTAP-containing formulation. The sequestering of nitric oxide by octafluoropropane, as well as the orders of magnitude increase in echogenicity and bioactive gas loading by changing the lipid constituent of the shell (without changing the lipid concentration) was not predicted. The same approach was also extended to produce Xe-loaded microbubbles for cerebrovascular applications.

As used herein, the term "acoustically responsive" refers to microbubbles that are echogenic, which refers to contrast on a B-mode ultrasound image, but which also vibrate in response to an acoustic wave. It is this vibration that triggers the release of encapsulated bioactive gas from the microbubble.

Microbubbles and Compositions

The present inventors have found that a perfluorocarbon gas as a trapped species or osmotic agent increases the stability of the microbubbles without significantly affecting the loading capacity. Surprisingly, it was also found that presence of the perfluorocarbon prevents diffusion of oxygen into the microbubbles, thereby reducing degradation of bioactive gas in situ—for example, the degradation of NO into nitrogen dioxide, $NO_2$, a pollutant. Combining a bioactive gas, such as NO, hydrogen sulfide, or xenon, with a perfluorocarbon gas, such as OFP, unexpectedly sequesters the bioactive gas within the phospholipid monolayer, thereby reducing its free diffusion into the surrounding media and preventing the corruption of the bioactive gas by oxygen diffusing into the microbubble.

Thus, certain embodiments provide an acoustically responsive microbubble comprising a phospholipid monolayer shell, an encapsulated bioactive gas selected from the group consisting of nitric oxide, hydrogen sulfide, and xenon gas, and an encapsulated perfluorocarbon gas of the formula $C_xF_y$, wherein X is greater than or equal to 3, and wherein the volume ratio of bioactive gas to $C_xF_y$ is from about 10:1 to about 1:10, including all values in the range. In a very specific embodiment, the ratio of bioactive gas to $C_xF_y$ is about 10:1.

In a specific embodiment, the perfluorocarbon gas is OFP, wherein X is 3 and Y is 8. However, the skilled artisan will appreciate that various perfluorocarbon gases are suitable for use in the present compositions and methods, including but not limited to perfluoropropane ($C_3F_8$), perfluorobutane ($C_4F_{10}$), perfluorocyclobutane ($C_4F_8$), perfluoropentane ($C_5F_{12}$), perfluorocyclopentane ($C_5F_{10}$), perfluoromethylcyclobutane ($C_5F_{10}$), perfluorohexane ($C_6F_4$), perfluorocyclohexane ($C_6F_{12}$), perfluoromethylcyclopentane ($C_6F_{12}$), perfluorodimethylcyclobutane ($C_6F_{12}$), perfluoroheptane ($C_7F_{16}$), perfluorocycloheptane ($C_7F_{14}$), perfluoromethylcyclohexane ($C_7F_{14}$), perfluorodimethylcyclopentane ($C_7F_{14}$), perfluorotrimethylcyclobutane ($C_7F_{14}$), and the like.

A variety of bioactive gases may be encapsulated in the presently disclosed microbubbles. In certain embodiments, the term "bioactive gas" refers to a bioactive gas selected from the group consisting of nitric oxide (NO), xenon (Xe), hydrogen sulfide ($H_2S$).

In some embodiments, the phospholipid monolayer shell comprises 1,2-distearoyl-sn-glycero-3-phosphocholine (DSPC) and 1,2-distearoyl-sn-glycero-3-phosphoethanolamine-N-[methoxy(polyethylene glycol)-2000] (DSPE-PEG 2000). The phospholipid monolayer in some embodiments is at least partially pegylated.

In other embodiments, it is desirable to incorporate target moieties into the phospholipid monolayer shell, in order to direct accumulation of the microbubbles at the target diseased section of vasculature. In such embodiments, the phospholipid monolayer shell is engineered to contain molecules that adhere to cells, which express disease-specific markers (e.g., amino acids) on the membrane. In this way, the microbubbles disclosed herein can be targeted to molecular components of disease by attaching specific target moieties to the surface of the phospholipid shell. Suitable target moieties include, but are not limited to, small-molecule ligands, peptides, proteins, and monoclonal antibodies.

For purposes of treating a subject in need of promoting vasodilation, acoustically responsive microbubbles are formulated into an intra venous (IV) composition and injected or otherwise administered to the subject at a site remote from the target treatment area, for example diseased cardiovascular tissue. In one specific embodiment, the target treatment area is monitored for presence of the acoustically responsive microbubbles and upon detection of presence, acoustic energy is applied sufficient to cause stable inertial or non-inertial cavitation depending on the clinical goal.

Preparation of liposomes or microbubbles into pharmaceutical-grade compositions formulated for IV administration is known in the art. In particular, Toh et al., *Liposomes as Sterile preparations and limitations of sterilization techniques in liposomal manufacturing, Asian Journal of Pharmaceutical Sciences,* 8(2):88-95 (April 2013) provides guidance for formulation of IV compositions of liposomes of the sizes of the microbubbles disclosed herein and provides useful guidance for formulation of compositions of the presently described microbubbles. The entire disclosure of Toh et al. is incorporated herein by this reference.

Methods of Promoting Vasodilation

In one embodiment a method for promoting vasodilation in a patient in need thereof is provided, the method comprising: delivering a microbubble comprising a phospholipid monolayer shell and an encapsulated bioactive gas locally to a target diseased section of the patient's vasculature; and releasing the bioactive gas at the target diseased section, wherein the microbubble comprises the bioactive gas in a volume ratio of from about 10:1 to about 1:10 with a perfluorocarbon gas. In a more specific embodiment, the volume ratio of bioactive gas to perfluorocarbon gas is about 10:1.

A variety of bioactive gases may be encapsulated in the presently disclosed microbubbles. In certain embodiments, the term "bioactive gas" refers to a bioactive gas selected from the group consisting of nitric oxide (NO), xenon (Xe), hydrogen sulfide ($H_2S$).

In some embodiments, delivering locally comprises administering the microbubble comprising the bioactive gas to the patient at a site remote from the target diseased section; monitoring for presence of the administered microbubble at the target diseased section; and upon detection of presence, administering acoustic energy to the target diseased section, thereby releasing a therapeutically effective amount of the bioactive gas from the microbubble to the target diseased section for a clinically relevant time frame.

The acoustic energy may be provided as continuous or pulsed waveforms. In specific embodiments the ultrasound is pulsed. In other more specific embodiments, rest periods wherein no ultrasound is delivered to the target area for a measurable amount of time may be incorporated into either continuous or pulsed ultrasound delivery. The rest periods may be patterned or sporadic. Such rest periods may provide opportunity for reperfusion of the target treatment area.

In certain embodiments, the perfluorocarbon gas has the formula $C_xF_y$, and X is greater than or equal to three. In a specific embodiment, the perfluorocarbon gas is OFP, wherein X is 3 and Y is 8.

In a specific embodiment, the phospholipid monolayer shell is at least partially pegylated and comprises 1,2-distearoyl-sn-glycero-3-phosphocholine (DSPC) and 1,2-distearoyl-sn-glycero-3-phosphoethanolamine-N-[methoxy (polyethylene glycol)-2000] (DSPE-PEG 2000).

In other embodiments, it is desirable to incorporate target moieties into the phospholipid monolayer shell, in order to direct accumulation of the microbubbles at the target diseased section of vasculature. In such embodiments, the phospholipid monolayer shell is engineered to contain molecules that adhere to cells, which express disease-specific markers (e.g., amino acids) on the membrane. In this way, the microbubbles disclosed herein can be targeted to molecular components of disease by attaching specific target moieties to the surface of the phospholipid shell. Suitable target moieties include, but are not limited to, small-molecule ligands, peptides, proteins, and monoclonal antibodies.

As noted above, the present methods are useful for promoting vasodilation in a patient in need thereof. Various cardiovascular diseases and conditions benefit from therapeutic treatment to promote vasodilation, including but not limited to, promotion of vasodilation in the brain or the heart, reduction of vasospasm in post traumatic brain injury, treatment of bacterial endocarditis, treatment of biofilm growth on an indwelling catheter or internal body surface, promotion of neuroprotection and reduction of reperfusion injury in the treatment of stroke, and promotion of cardioprotection and reduction of reperfusion injury in the treatment of myocardial infarction. Promoting vasodilation may also reduce the risk of certain other undesirable medical conditions. In some embodiments, the antiproliferative effects of NO reduce risk of neointimal hyperplasia post stent deployment or within an arteriovenous fistula for dialysis access.

According to another embodiment, a method for preventing passive diffusion of a bioactive gas from a microbubble into a non-target tissue or fluid is provided, the method comprising encapsulating the bioactive gas with a perfluorocarbon gas of the formula $C_xF_y$, wherein X is greater than or equal to three and wherein a volume ratio of bioactive gas to perfluorocarbon gas is from about 10:1 to about 1:10.

Preparation of a Microbubble Suspension

In specific manufacturing embodiments, the methods comprise: providing a lipid dispersion comprising phospholipids in a sealed receptacle such as a glass vial, evacuating air from a headspace of the sealed receptacle, injecting a volume ratio of a bioactive gas and a perfluorocarbon gas of the formula $C_xF_y$, into the headspace; and subjecting the receptacle to high-shear mixing, thereby providing a suspension comprising microbubbles loaded with the bioactive gas. In methods known in the prior art, freezing of a lipid emulsion was considered to be a necessary step for achieving encapsulation of gases and/or other agents at desired volumes. According to embodiments provided herein, freezing of the lipid dispersion is utilized simply to remove the residual solvents during lipid film preparation. Instead, high shear mixing is used to generate lipid-encapsulated microbubbles.

In certain embodiments, the volume ratio of bioactive gas to perfluorocarbon gas is from about 10:1 to about 1:10. In very specific embodiments, X is 3, F is 8 ("OFP"), and the ratio of bioactive gas:OFP is 10:1.

According to specific embodiments, the lipid dispersion comprises a mixture of phospholipids. According to very specific embodiments, the lipid dispersion formulation comprises: DSPC (1,2-distearoyl-sn-glycero-3-phosphocholine)

and DSPE-PEG 2000 (1,2-distearoyl-sn-glycero-3-phosphoethanolamine-N-[methoxy(polyethylene glycol)-2000] dispersed in a solution containing phosphate buffered saline:propylene glycol:glycerol in a molar ratio of 16:3:1, with a final lipid concentration of 1 mg/mL. As shown in the examples, stability of this formulation was demonstrated at physiologic temperature. It was found that microbubbles comprising DSPC encapsulate orders of magnitude higher gas payload than formulations comprising DOTAP. The sequestering of NO gas by OFP gas, as well as the orders of magnitude increase in acoustic responsiveness and bioactive gas loading observed in microbubbles comprising DSPC without changing the lipid concentration was unexpected. Similar results were observed in xenon-loaded microbubbles for cerebrovascular applications.

Quantifying Bioactive Gas Load

Also provided herein are methods for quantifying an amount of nitric oxide gas encapsulated within microbubbles in a suspension, the method comprising: providing a known volume of a suspension comprising microbubbles encapsulating nitric oxide; transferring the suspension into degassed phosphate buffered saline; stirring the suspension continuously to release the nitric oxide from the microbubbles into the phosphate buffered saline; measuring the nitric oxide dissolved in the phosphate buffered saline to determine total nitric oxide in the suspension; and comparing the total nitric oxide in the suspension to a control value to quantify the amount of nitric oxide encapsulated within the microbubbles of the suspension.

Methods for quantifying an amount of xenon encapsulated within microbubbles in a suspension are also provided, the method comprising: providing a known volume of a suspension comprising microbubbles encapsulating xenon in a sealed receptacle such as a glass vial; sonicating the receptacle; measuring the amount of xenon in a headspace of the receptacle to determine total xenon in the suspension; comparing the total xenon in the suspension to a control value to quantify the amount of xenon encapsulated within the microbubbles of the suspension. In a specific embodiment, the amount of xenon in the headspace of the receptacle is measured by gas chromatography-mass spectrometry (GC-MS).

The following Examples are set forth to illustrate particular embodiments of the invention and should not be construed as limiting the full scope of the invention as defined by the claims and understood by a person of skill in the art.

EXAMPLES

Example 1

Preparation of Bioactive Gas-Encapsulating Microbubbles

Bioactive gas-loaded microbubble agents were developed that encapsulated 1) Nitric Oxide (NOMB), and 2) Xenon (XeMB). These agents were encapsulated by a phospholipid shell with a PEG coating. Briefly, DSPC (1,2-distearoyl-sn-glycero-3-phosphocholine) and DSPE-PEG 2000 (1,2-distearoyl-sn-glycero-3-phosphoethanolamine-N-[methoxy (polyethylene glycol)-2000] were dissolved at a molar ratio of 9:1 chloroform and the solution was evaporated to form a thin film. The thin-film was dried overnight under vacuum using a lyophilizer. The film was rehydrated using a solution containing phosphate buffered saline:propylene glycol:glycerol (16:3:1), which resulted in a final lipid concentration of 1 mg/mL. This solution was sonicated in a bath sonicator for 45 minutes to obtain clear lipid dispersion. Glass vials (2-mL volume) were aliquoted with 1 mL of lipid dispersion, sealed using Teflon/ptfe caps and the headspace was evacuated using a laboratory vacuum. Either Nitric Oxide or Xenon (1 mL) was injected into the headspace of each vial. The vials were activated by high-shear mixing for 45 s using a Vialmix (Lantheus, N. Billerica, Mass., USA), which produced in a cloudy suspension containing microbubbles loaded with either bioactive gas.

Example 2

Attenuation Spectroscopy

Figure 1:
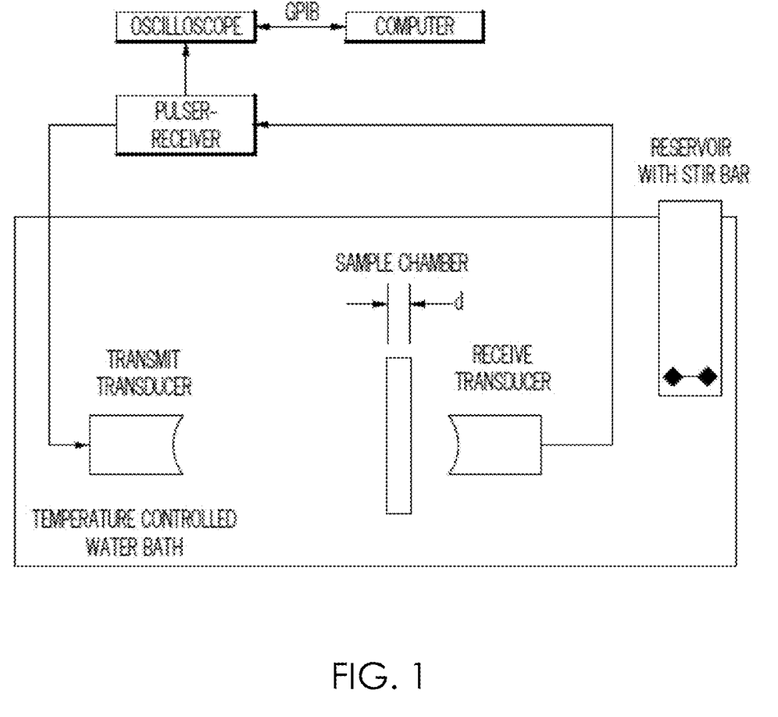
Figure 2:
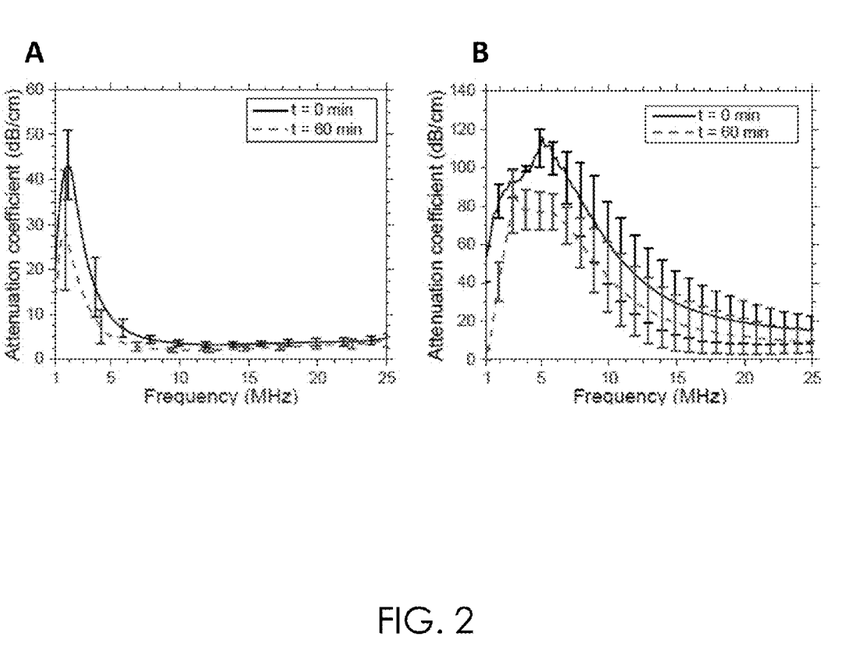
FIG. 2. Attenuation spectra of (A) nitric oxide-loaded microbubbles, and (B) xenon-loaded microbubbles. In each case, microbubbles remained attenuative even after 60 minutes, demonstrating stability of the formulations.

Attenuation spectroscopy was used to confirm the encapsulation of gas within the microbubbles formulation, as well as assess the stability of gas-encapsulated microbubbles over time. Set-up is depicted in FIG. 1. The frequency-dependent attenuation coefficient was measured using a broadband substitution technique as described previously (Raymond et al 2014). After the gas-loaded microbubbles were manufactured, they were diluted in 0.5% (w/v) bovine serum albumin (a blood-mimicking fluid) and their attenuation spectrum over the frequency range 2-25 MHz was measured over 60 minutes. The microbubbles continued to attenuate ultrasound over 60 minutes, which highlights the ability of the present formulation to keep bioactive gas sequestered for a clinically relevant time frame. FIG. 2 shows attenuation spectra of (A) nitric oxide-loaded microbubbles, and (B) xenon-loaded microbubbles. In each case, microbubbles remained attenuative even after 60 minutes, demonstrating stability of the formulations.

Example 3

Size Distribution Assessment

Figure 3:
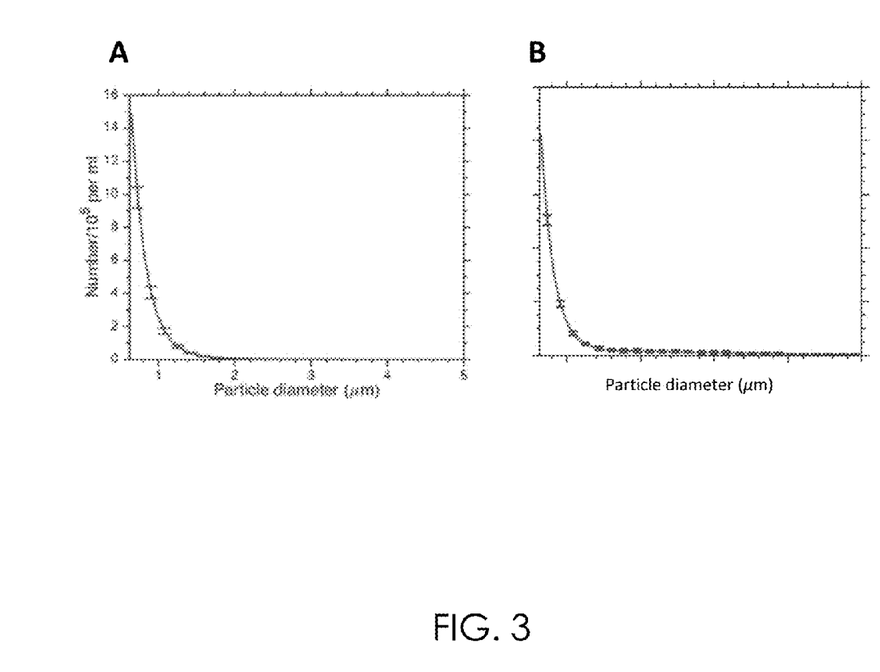
FIG. 3. Number-weighted size distribution of (A) nitric oxide-loaded microbubbles (NOMB), and (B) xenon-loaded microbubbles (XeMB). In each case, the microbubbles were small enough to pass through the capillaries of the lung.

Bioactive gas-loaded microbubbles were diluted in phosphate buffered saline and their size distribution was measured using a Coulter counter (Multisizer 4, Beckman Coulter, Brea, Calif., USA) to produce number-weighted size distributions. For both formulations (NOMB and XeMB), over 99.9% of microbubbles were smaller than 7 µm (FIG. 3), which will facilitate passage through the capillaries of the lung and prevent microemboli. FIG. 3 shows number-weighted size distribution of (A) nitric oxide-loaded microbubbles (NOMB), and (B) xenon-loaded microbubbles (XeMB). In each case, the microbubbles were small enough to pass through the capillaries of the lung.

Example 4

Feasibility of Ultrasound-Mediated Release

Figure 4:
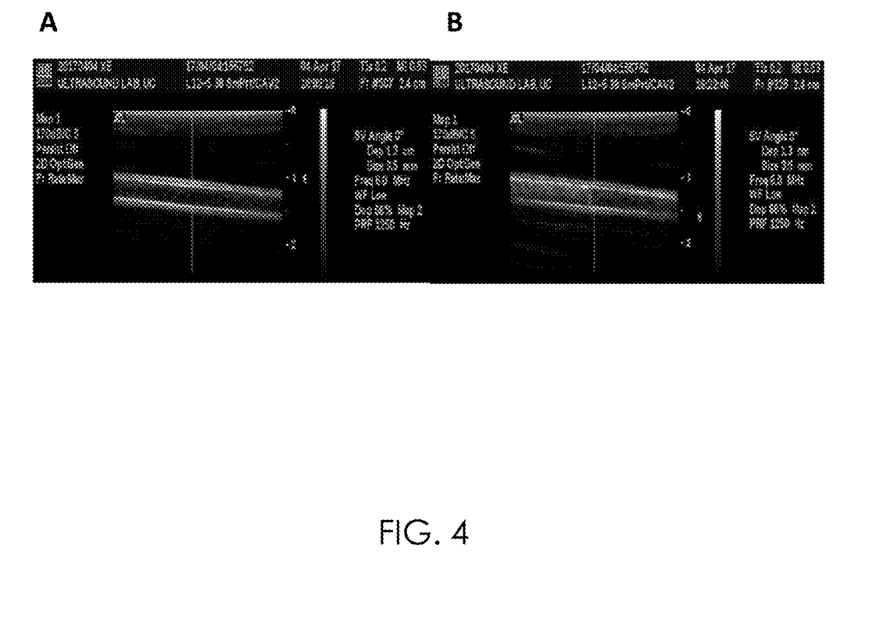
FIG. 4. B-mode ultrasound image of a latex tube filled with (A) 0.5% BSA only, and (B) 0.5% BSA with XeMB. The direction of flow is from left to right. The destruction of XeMB at the site of Doppler ultrasound insonation is apparent, showing the feasibility of ultrasound-mediated gas delivery.

To assess the feasibility of ultrasound-mediated release, XeMB were exposed to Doppler Ultrasound pulses (center frequency=6 MHz, mechanical index=0.53, sample volume=1 mL). FIG. 4 shows a B-mode ultrasound image of the longitudinal section of a latex tube perfused with 0.5% BSA in a water tank. The lumen on the tube is hypoechoic. However, when XeMB was perfused into the system, the lumen became hyperechoic due to scattering from the Xenon-loaded microbubbles. The microbubbles were destroyed upon exposure to Doppler ultrasound, which demonstrated the feasibility of ultrasound-mediated release of bioactive gases

Example 5

Quantification of Nitric Oxide Encapsulated within Nitric Oxide-Loaded Microbubbles (NOMB)

The amount of NO encapsulated within NOMB was measured using a calibrated amperometric probe (TBR4100, World Precision Instruments, Sarasota, Fla.). Specifically, a known volume of NOMB suspension was transferred into degassed phosphate buffered saline (PBS) held in a glass container at 37° C. The PBS was either air saturated or degassed ($pO_2$=40%), and stirred continuously using a magnetic stirrer. Microbubbles are known to be stable in air-saturated PBS. On the contrary, degassed PBS is known to force the diffusion of NO from NOMB into the PBS. The concentration of dissolved NO in solution was measured using the calibrated probe. This measurement provided the total concentration of NO in the NOMB suspension. To measure the amount to NO that is encapsulated in microbubbles, a subtraction-based approach was followed. Specifically, the concentration of NO was measured with the NOMB diluted in air-saturated PBS (See FIG. 5, Intact NOMB). The amount of NO measured was considered as background. The amount of NO encapsulated was calculated by subtracting the background from the total concentration of NO measured by breaking NOMB.

Figure 5:
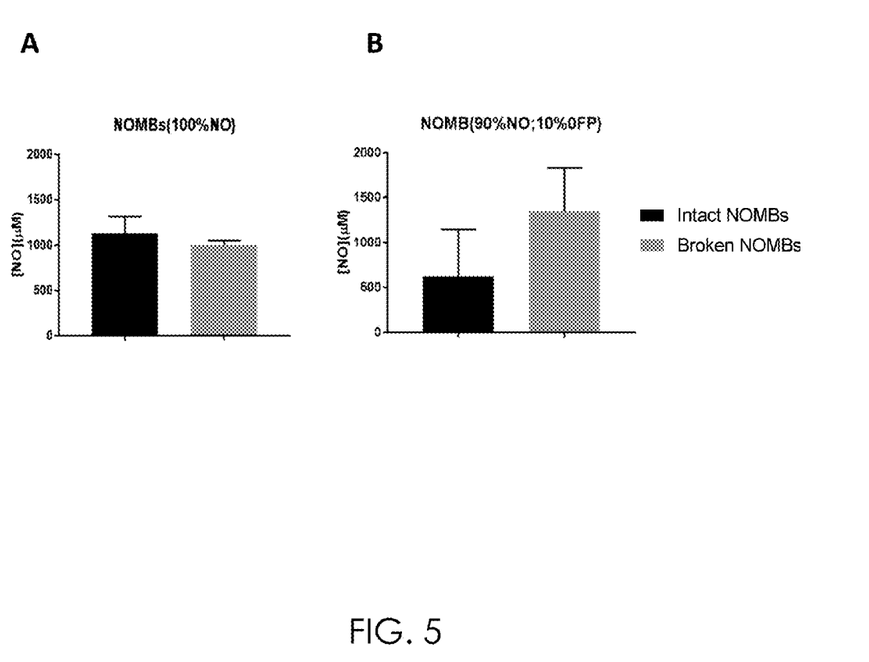

To test the role of octafluoropropane (OFP) in stabilizing NOMB osmotically, NOMB were prepared by injecting 1 ml of gas (either 100% NO or 90% NO and 10% OFP (v/v)) in the vial headspace followed by high-shear mixing. When NOMB were prepared with 100% NO gas, no difference was found between the background and total NO measurement (FIG. 5(A)), likely because all NO diffused out almost instantaneously from the microbubble into the solution. However, when NOMB were prepared by adding the NO/OFP gas mixture, the amount of NO encapsulated within NOMB was found to be nearly 0.7 mM. These results show that adding a small percentage of OFP by volume is critical to encapsulating NO within NOMB (FIG. 5(B)).

Example 6

Quantification of Xenon Encapsulated Inside XeMB

A known volume of Xenon encapsulated microbubbles (XeMB) was transferred to a capped glass vial. The vial was submerged in a bath and sonicated at 40-kHz frequency for 5 min to release the entire payload of Xe from XeMB. The amount of Xe released was measured using headspace analysis with a mass spectrometer (5973A, The Hewlett-Packard Company) interfaced with a gas chromatograph (Model 6890, Hewlett-Packard Company). The difference in Xe concentration measured with and without sonication was used to quantify the volume of gas encapsulated per milligram of lipid within XeMB. The results revealed that XeMB encapsulated 800/mg of xenon per milligram of lipid, which is at least four-fold higher than the previously reported xenon-loaded echogenic liposome formulations.

Example 7

Ultrasound-Mediated Release of Xe from XeMB

Figure 6:
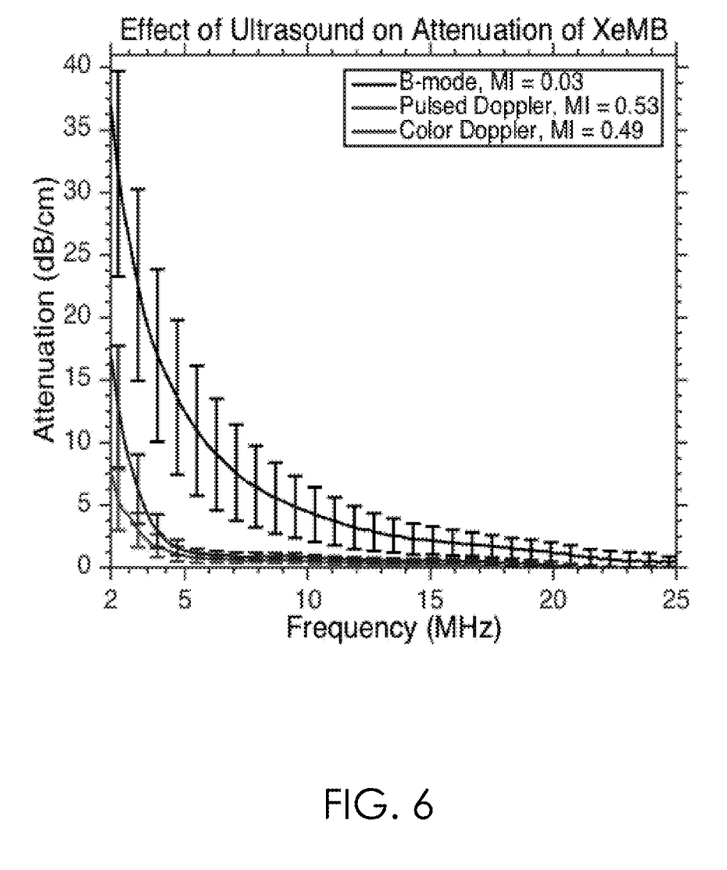
FIG. 6. Attenuation spectroscopy measurements of the effluent obtained after insonification of XeMB.

Assessment of the acoustic response of XeMB is important for ultrasound-mediated release of xenon. The acoustic response of XeMB was evaluated using an attenuation spectrometer. Specifically, the XeMB suspension was diluted 1000-fold using 0.5% bovine serum albumin and allowed to flow into a Clinicell® (CLINIcell® 25, Mabio, Tourcoing, France) through a latex tube (5 mm diameter) at a flow rate of 5 ml/min. The latex tube was exposed to ultrasound using a commercial ultrasound system (HDI 5000, Philips). Three insonation different modes were tested on XeMB individually and attenuation spectroscopy studies were performed with the effluent. FIG. 6 shows the attenuation coefficients of the effluents collected after XeMB were insonified under three different modes (B-mode, Color Doppler, and Pulsed Doppler). B-mode imaging was performed at a very low Mechanical Index (0.03) as a negative control for Xe release. Pulsed and color Doppler were used at mechanical indices of 0.53 and 0.49, respectively to try to induce the release of Xe from XeMB. The sample volume used for pulsed Doppler ultrasound was 1 ml. In response to both Doppler ultrasound modes, the attenuation coefficient dropped by almost 20-30 dB, which suggests that Xe was released from XeMB.

Example 8

Stability of XeMB when Injected Through 19-Guage and 25-Gauge Needles

Figure 7:
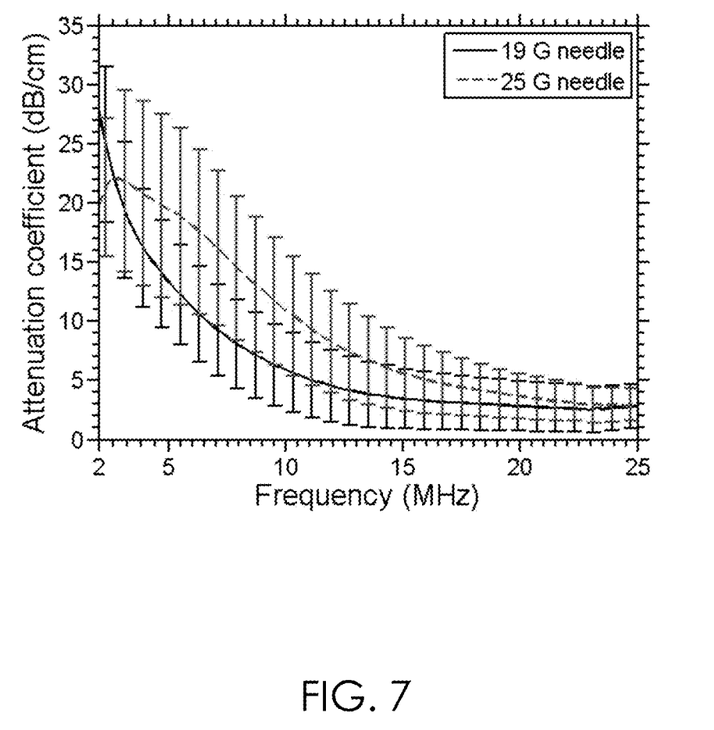
FIG. 7. Attenuation spectrum of XeMB effluent injected through 19-gauge and 25-gauge needles.

Stability of XeMB was studied when injected through a 19-gauge and 25-gauge needle at a flow-rate of 4 ml/min and 0.2 ml/min, respectively. These flow rates mimic the flow rates used clinically and in preclinical studies for ultrasound contrast agents. The effluent was collected and the attenuation coefficient of the suspension measured. The results revealed that the XeMB attenuation coefficient measured after injection through a 25-gauge needle was within one standard deviation of that measured using a 19-gauge needle. See FIG. 7. These results suggest that XeMB can be injected using either a 19-gauge or a 25-gauge needle based on the intended application.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise. Methods can include a step of providing a subject suffering from a disease or condition that benefits from therapeutically promoting vasodilation, a step of diagnosing a subject as having a disease or condition that benefits from therapeutically promoting vasodilation (such as cardiovascular disease), and/or a step of selecting a subject for which an inventive product or method would be suitable.

Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention, or any combination thereof, may be explicitly excluded from any one or more claims whether or not such exclusion is expressly recited herein. For example, any lipid shell or encapsulated gas component ingredient, etc., can be explicitly excluded. Applicants reserve the right to proviso out of the claims any specific component, component category, or combination thereof, whether or not such component, category, or combination thereof, is recited herein. To the extent, if any, that a echogenic liposome that is known or described in the prior art may include nitric oxide, the instant invention may be distinguished from such prior art liposome or methods utilizing such prior art liposome in, for example, any one or more of the following ways: (i) the acoustically responsive microbubbles of the invention comprises one or more gases or lipid shell components or configurations (e.g., monolayer phospholipid shell) not present in the prior art liposome or microbubble; (ii) the acoustically responsive microbubble of the invention comprises a different amount of specific components, or a specific ratio of specific components, not recognized or appreciated as significant to utility or efficacy in the prior art liposome or microbubble and methods; or (iii) the acoustically responsive microbubble or methods of the invention omit at least one ingredient present and considered necessary in the prior art liposome or microbubble or methods.

What is claimed:

1. An acoustically responsive microbubble comprising:
   a phospholipid monolayer shell comprising 1,2-distearoyl-sn-glycero-3-phosphocholine (DSPC) and 1,2-distearoyl-sn-glycero-3-phosphoethanolamine-N-[methoxy(polyethylene glycol)-2000] (DSPE-PEG 2000),
   an encapsulated bioactive gas selected from the group consisting of nitric oxide, xenon gas, and hydrogen sulfide, and
   an encapsulated perfluorocarbon gas of the formula $C_xF_y$, wherein X=3 and Y=8, and wherein a volume ratio of bioactive gas to $C_xF_y$ is from about 10:1 to about 1:10.

2. The acoustically responsive microbubble according to claim 1, wherein the ratio of bioactive gas to $C_xF_y$ is about 10:1.

3. The acoustically responsive microbubble according to claim 1, wherein the phospholipid monolayer shell further comprises target moieties for directing accumulation of the microbubbles at a target diseased section of a patient's vasculature.

4. A method for promoting vasodilation in a patient in need thereof, the method comprising:
   delivering the acoustically responsive microbubble according to claim 1 locally to a target diseased section of the patient's vasculature; and
   releasing the bioactive gas at the target diseased section.

5. The method according to claim 4, wherein delivering locally comprises administering the microbubble comprising the bioactive gas to the patient at a site remote from the target diseased section; and administering acoustic energy to the target diseased section, thereby releasing a therapeutically effective amount of the bioactive gas from the microbubble to the target diseased section for a clinically relevant time frame.

6. The method according to claim 5, further comprising monitoring for presence of the administered microbubble at the target diseased section prior to administering acoustic energy to the target diseased section, wherein acoustic energy is administered upon detection of presence of the administered microbubble.

7. The method according to claim 4, wherein the phospholipid monolayer shell further comprises target moieties for directing accumulation of the microbubbles at the target diseased section.

8. The method according to claim 4, wherein the patient is suffering from a condition selected from the group consisting of cardiovascular disease, cerebrovascular disease, vasospasm post traumatic brain injury, bacterial endocarditis, biofilm growth on an indwelling catheter or internal body surface, and maintenance of arteriovenous fistula for dialysis access.

9. The method according to claim 4, wherein antiproliferative effects of nitric oxide reduce risk of neointimal hyperplasia post stent deployment or promote patency in an arteriovenous fistula for dialysis access.

10. A method of manufacturing the acoustically responsive microbubble according to claim 1, the method comprising:
    providing a lipid dispersion comprising phospholipids in a sealed receptacle;
    evacuating air from a headspace of the sealed receptacle;
    injecting a volume ratio of a bioactive gas and a perfluorocarbon gas of the formula $C_xF_y$ into the headspace; and
    subjecting the receptacle to high-shear mixing.

* * * * *